US00PP31996P2

(12) United States Plant Patent
Davasse

(10) Patent No.: US PP31,996 P2
(45) Date of Patent: Jul. 21, 2020

(54) ***SPIRAEA* 'DAVCOP01'**

(50) Latin Name: ***Spiraea japonica* x *bumalda***
Varietal Denomination: DAVCOP01

(71) Applicant: Jean-Paul Davasse, Angers (FR)

(72) Inventor: Jean-Paul Davasse, Angers (FR)

( * ) Notice: Subject to any disclaimer, the term of this patent is extended or adjusted under 35 U.S.C. 154(b) by 0 days.

(21) Appl. No.: 16/501,788

(22) Filed: Jun. 6, 2019

(51) Int. Cl.
*A01H 5/00* (2018.01)
*A01H 6/74* (2018.01)

(52) U.S. Cl.
USPC ..... Plt./226

(58) Field of Classification Search
USPC ..... Plt./226
CPC ..... A01H 5/00
See application file for complete search history.

(56) References Cited

PUBLICATIONS

PLUTO Plant Variety Database Dec. 17, 2019. p. 1.*

* cited by examiner

*Primary Examiner* — Annette H Para
(74) *Attorney, Agent, or Firm* — Cassandra Bright

(57) ABSTRACT

'DAVCOP01' is a new cultivar of hybrid *Spiraea* with distinctive copper emerging foliage. Plants are compact and attractively rounded. Summer foliage is bright yellow-green, this bright coloration is maintained throughout the Summer. The new variety is a *Spiraea* normally produced as an outdoor garden or container plant.

5 Drawing Sheets

Latin name of the genus and species: *Spiraea japonica* x *bumalda*.
Title: *Spiraea* 'DAVCOP01'.

BACKGROUND OF THE INVENTION

The present invention comprises a new and distinct hybrid *Spiraea* cultivar hereinafter referred to by the cultivar name 'DAVCOP01'. This new *Spiraea* was developed through a breeding program in Angers, France. 'DAVCOP01' was selected from a population of seedlings grown from a controlled cross. The controlled cross was made July of 2010. The seed parent is *Spiraea japonica* 'Baicarol', unpatented. The pollen parent is *Spiraea bumalda* 'Denistar' U.S. Plant Pat. No. 22,432. The first asexual propagation of 'DAVCOP01' was carried out in May 2014 by rooting stem cuttings at a research nursery in Angers, France, and has been asexually reproduced repeatedly by vegetative cuttings over a 5-year period. 'DAVCOP01' has been found to retain its distinctive characteristics through successive asexual propagations.

SUMMARY OF THE INVENTION

The following are the unique combination of characteristics of this new cultivar when grown under standard horticultural practices at a research greenhouse in Angers, France.

1. Very round plants.
2. Copper colored emerging foliage.
3. Bright yellow-green foliage, maintain this color all Summer.
4. Some resistance to powdery mildew.

COMPARISON TO PARENTAL VARIETIES

'DAVCOP01' is similar to its female parent in most horticultural characteristics, however, the new variety differs in the following:

1. Coloration of the emerging foliage of 'DAVCOP01' is bronze, coloration of the emerging foliage of the seed parent is light yellow-green.
2. Mature foliage color of the new variety is bright yellow-green, the mature foliage color of the seed parent is green.
3. Peduncles of the new variety are darker than those of the seed parent.

'DAVCOP01' is similar to its male parent in most horticultural characteristics, however, the new variety differs in the following:

1. Plant habit of the new variety is overall smaller, more compact and rounder than that of the pollen parent.
2. Mature foliage color of the new variety is bright light yellow-green, mature foliage color of the pollen parent is green.
3. Flower color of the new variety is darker pink than flower color of the pollen parent.

COMPARISON WITH COMMERCIAL CULTIVARS

'DAVCOP01' can be compared to the commercial variety *Spiraea* 'Goldflame', unpatented. The two *Spiraea* are similar in most horticultural characteristics. The new variety, however differs in the following:

1. The new variety is more compact, and forms rounder plant than this comparator.
2. Foliage of the new variety is smaller than that of this comparator.
3. Coloration of the emerging foliage of 'DAVCOP01' is a deeper, more pronounced bronze color than that of this comparator.

BRIEF DESCRIPTION OF THE DRAWINGS

This new *Spiraea* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new hybrid *Spiraea*.

DETAILED BOTANICAL DESCRIPTION

Figure 1:
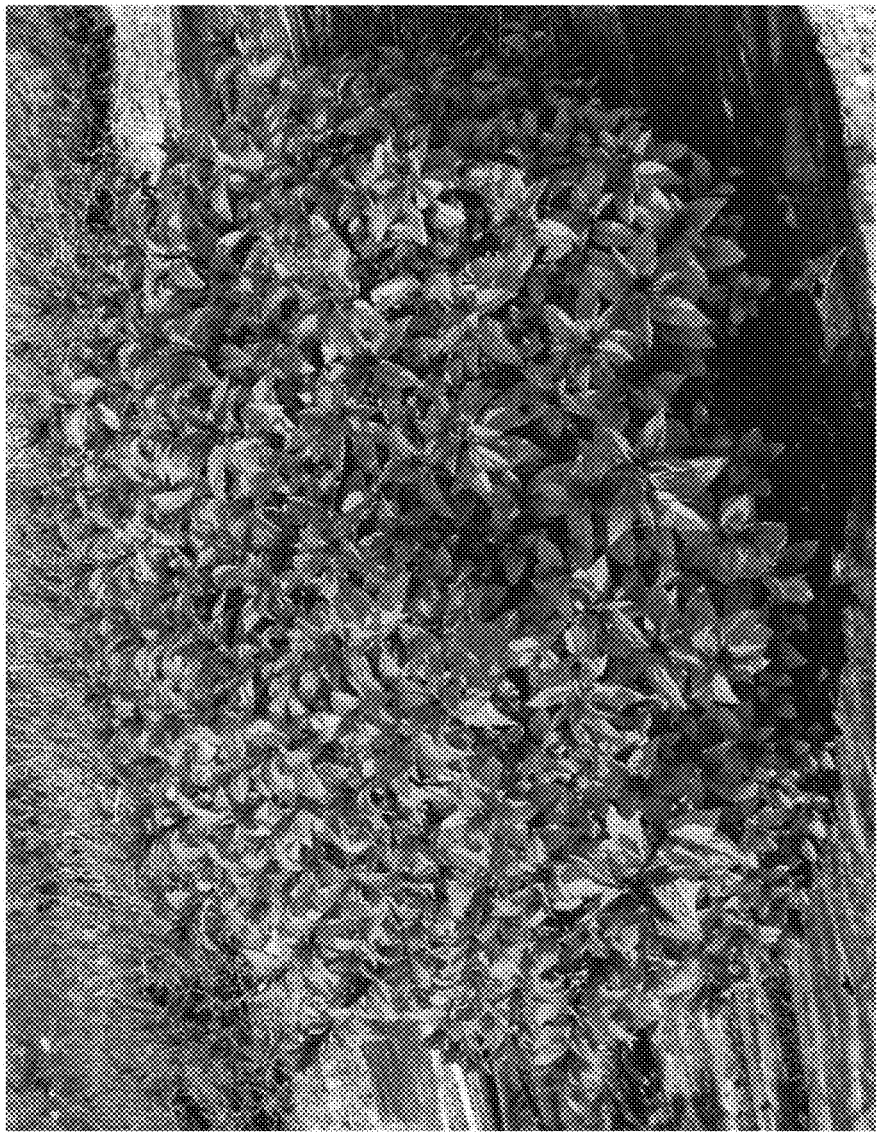
FIG. 1 is a color photograph showing a plant of 'DAVCOP01' in Angers, France during late April 2018, with emerging foliage coloration. The plant is approximately 2.5 years old, planted in the ground.
Figure 2:
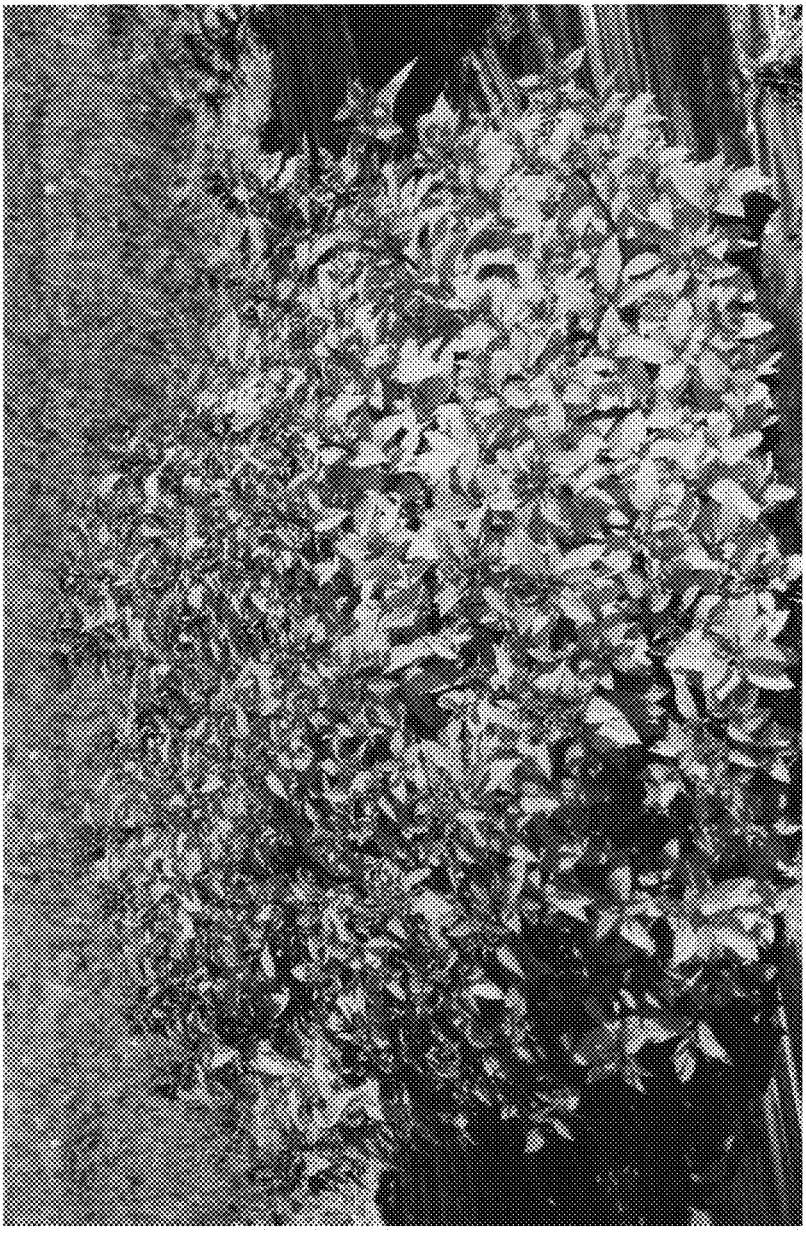
FIG. 2 is a of the same plant as FIG. 1, approximately 4 to 6 weeks later with early Summer foliage and inflorescences developing.
Figure 3:
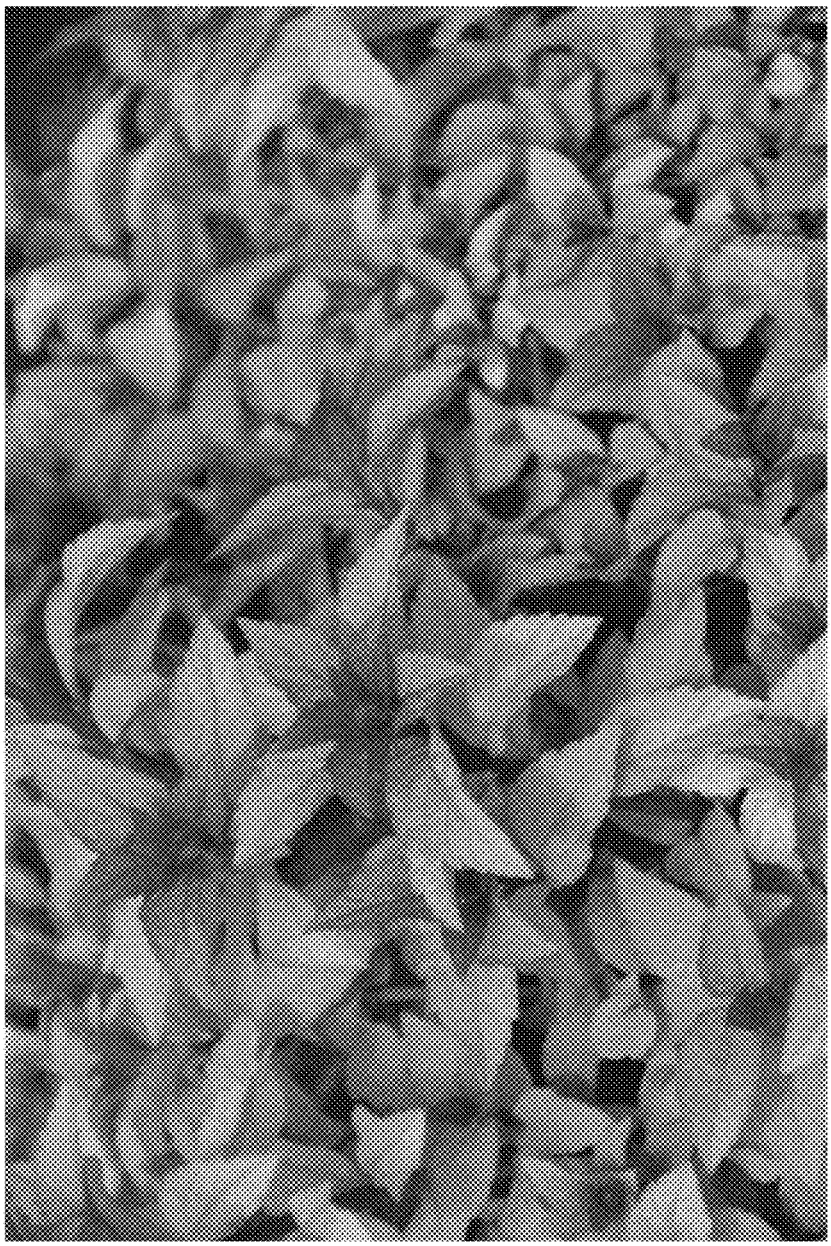
FIG. 3 is a color photograph showing a close-up view of emerging foliage.
Figure 4:
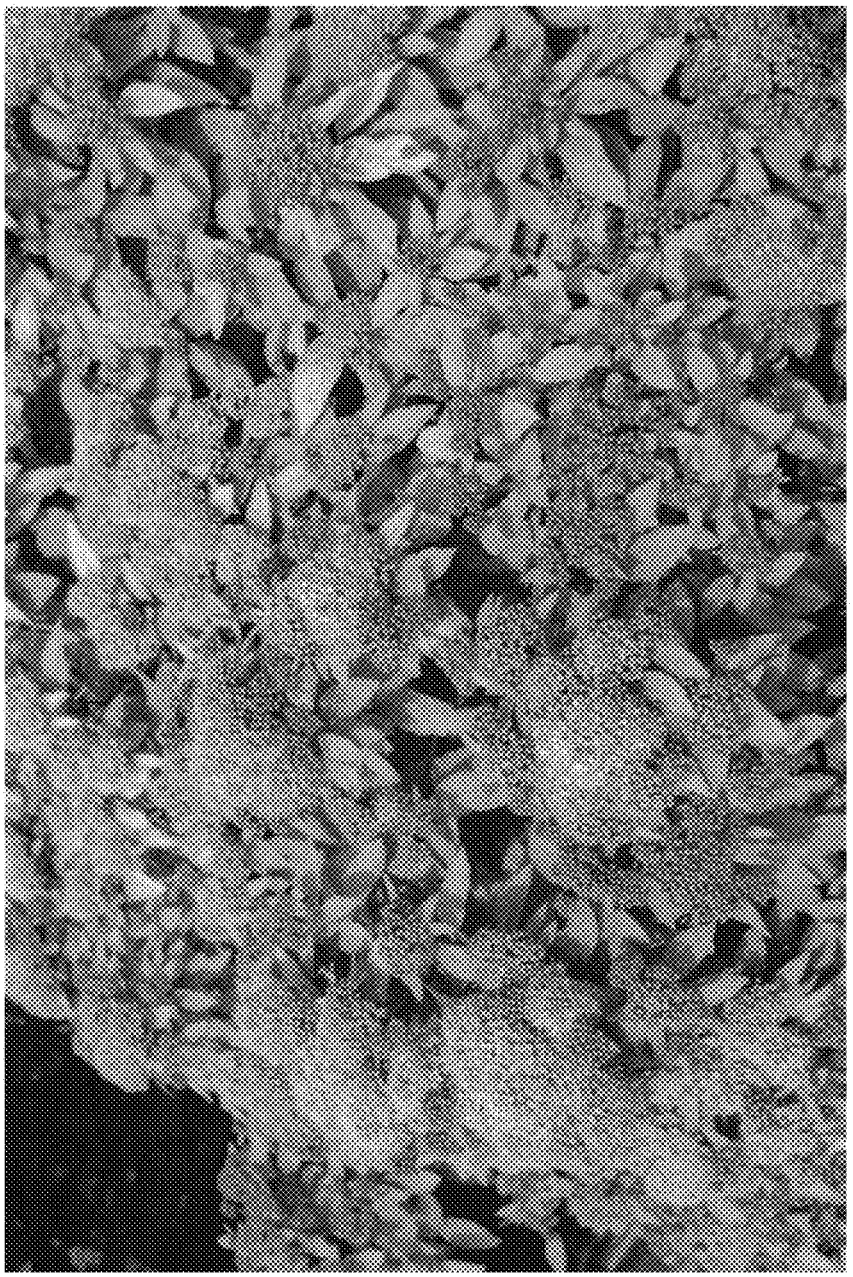
FIG. 4 shows inflorescences and mature foliage of 'DAVCOP01' in Angers, France.
Figure 5:
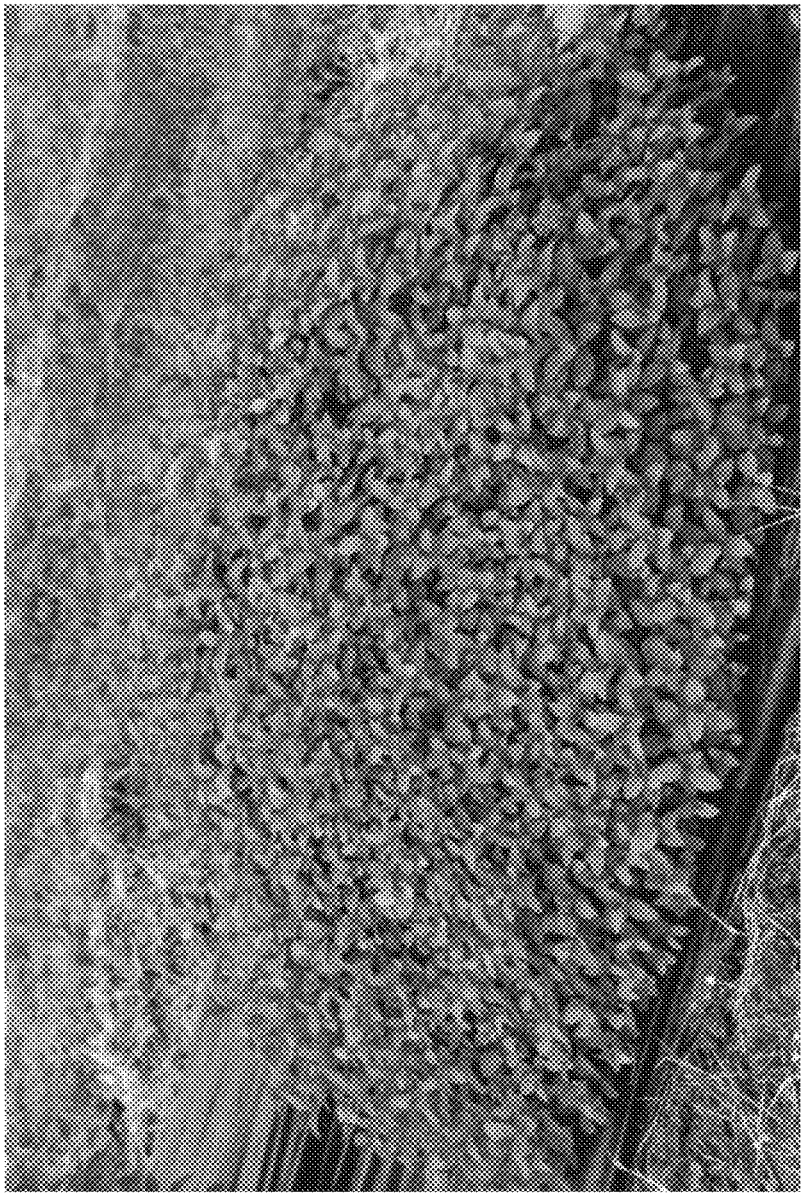
FIG. 5 is a of the same plant as FIG. 1 and FIG. 2, with late Summer foliage and more developed inflorescences.

The following is a detailed description of the botanical characteristics of the new and distinct hybrid *Spiraea* known by the denomination 'DAVCOP01'. The detailed description was taken on a three-year-old field-grown plant in Angers, France. All colors cited herein refer to The Royal Horticultural Society Colour Chart (The Royal Horticultural Society (R.H.S.), London, 2007 Edition. Where specific dimensions, sizes, colors, and other characteristics are given, it is to be understood that such characteristics are approximations or averages set forth as accurately as practicable.

Botanical classification: *Spiraea japonica* x *bumalda* 'DAVCOP01'.

Plant description:

*Habit*.—Rounded/mounded woody deciduous shrub.

*Height*.—About 75 cm.

*Width*.—About 95 cm.

Branches: Average 4 per main stem.

*Lateral branch diameter*.—1 to 1.5 cm.

*Lateral branch length*.—40 to 65 cm.

*Internode length*.—1 to 2 cm.

*Branch color*.—Immature: RHS Greyed-Purple 183A. Mature: RHS Greyed-Orange 178C.

*Branch texture*.—Finely striated.

Leaves:

*Type*.—Simple.

*Persistence*.—Deciduous.

*Arrangement*.—Alternate.

*Shape*.—Ovate.

*Apex*.—Acute.

*Base*.—Acute.

*Margins*.—Serrate to crenate.

*Color*.—Emerging leaves, upper surface: RHS Greyed-Purple 185A, lower surface: 183B. Young leaves: upper surface: RHS Greyed-Orange N167B flushed Greyed-Purple 183B. Lower surface: RHS Greyed-Orange N167C flushed 183C. Mature leaves: Upper and lower surface RHS Yellow-Green N144B. Texture: Glabrous. Length of lamina: Average 3.0 cm. Width: Average 2.3 cm.

*Venation*.—Pinnate.

*Vein color*.—Emerging leaves, upper surface: RHS Greyed-Purple 185A, lower surface: 183A. Young leaves: upper surface: RHS Greyed-Purple 183B. Lower surface: Greyed-Red 181A. Mature leaves: Mid Veins Upper surface: RHS Yellow-Green 144. Mid Veins Lower surface: RHS Greyed-Orange N172D. Lateral Veins: Upper and lower surface RHS Yellow-Green N144B.

*Leaf attachment*.—Petiolate.

*Petiole*.—Length: Average 5 to 7 mm. Diameter: 1 mm. Color: Emerging leaves: RHS Greyed-Purple 185A. Young leaves: RHS Greyed-Red 180B. Mature leaves: RHS Yellow-Green N144B. Texture: Glabrous.

Inflorescence:

*Description*.—Single whorled, rotate flowers arranged on a terminal corymb.

*Number of flowers per inflorescence*.—About 120 to 200.

*Flowering season*.—Spring and Summer in Angers, France.

*Inflorescence diameter*.—7-8 cm.

*Inflorescence height*.—About 5 cm.

*Bud*.—Shape: Globular. Length: about 2 mm. Diameter: about 2 mm. Color: Greyed-Purple N187A.

*Flower*.—Diameter: about 5 to 6 mm. Height: About 3 mm. Flower aspect: Upward and outwardly facing.

*Petal*.—Arrangement: Whorl. Number: 5. Fused: Not fused. Texture: Glabrous, all surfaces. Shape: Orbicular Margin: Entire. Apex: Obtuse. Base: Obtuse. Length: 2 to 3 mm. Width: about 2 mm. Color when opening. Upper surface: RHS Red-Purple 71B. Lower surface: Near RHS Purple 77C, margin 77A. Color at maturity: Upper surface: RHS Red-Purple 70A. Lower surface: Near RHS Purple 77B, margin 77A. Color when fading: Upper surface: RHS Red-Purple 70C, margins 70B. Lower surface: Near RHS Purple 77D, margin 77B.

*Calyx*.—Shape: Cup-shaped with five lobes. Length: About 3 mm. Diameter: About 2 mm.

*Sepal*.—Arrangement: Single whorl. Number: 5. Texture: Pubescent along margins. Shape: Acute. Margin: Entire. Apex: Acute. Base: Fused. Color: Near RHS Green 137B margins lightly flushed Purple 77A. Length: About 1.5 mm. Width: About 1 mm.

*Peduncle*.—Length: About 1.9 to 3.8 mm. Diameter: About 8 to 10 mm. Color: Near RHS Greyed-Purple 183C. Texture: Glabrous.

*Pedicels*.—Length: 5 to 7 mm. Diameter: About 1 mm. Color: Near RHS Greyed-Purple 185B. Texture: Glabrous.

Reproductive organs:

*Gynoecium*.—Pistil number: 5. Pistil length: 3 mm. Stigma shape: linear. Stigma color: Near RHS Purple N77A. Style length: 2 mm. Style color: Near RHS Purple 77C. Ovary color: Near RHS Yellow-Green 144C.

*Androecium*.—Stamen number: 10 to 20. Anther shape: Linear. Anther size: 1 mm. Anther color: Near RHS Red-Purple 71A. Filament length: 3 to 5 mm. Filament color: Near RHS Red-Purple 70B. Amount of pollen: Scant. Pollen color: RHS Purple 76D.

OTHER CHARACTERISTICS

Fruit and seed: Not observed to date.

Disease and insect resistance: Some tolerance for powdery mildew observed. Neither resistance nor susceptibility to other normal diseases and pests has been observed.

Temperature tolerance: USDA Zones 4 to 8. Cold hardy to at least −25° C.

What is claimed is:

1. A new and distinct hybrid *Spiraea* plant named 'DAVCOP01' substantially as illustrated and described herein.

* * * * *